US011938504B2

(12) United States Patent
Santamaría Ramiro et al.

(10) Patent No.: US 11,938,504 B2
(45) Date of Patent: Mar. 26, 2024

(54) NANOPARTICULATE-AEROSOL GENERATOR AND METHOD FOR CONTINUOUSLY GENERATING AEROSOLS, ASSOCIATED WITH SAID GENERATOR

(71) Applicant: Universidad de Zaragoza, Saragossa (ES)

(72) Inventors: Jesús Santamaría Ramiro, Saragossa (ES); Francisco Balas Nieto, Saragossa (ES); Maria Pilar Lobera González, Saragossa (ES); Alberto Clemente Cornago, Saragossa (ES)

(73) Assignee: UNIVERSIDAD DE ZARAGOZA, Saragossa (ES)

( * ) Notice: Subject to any disclaimer, the term of this patent is extended or adjusted under 35 U.S.C. 154(b) by 1145 days.

(21) Appl. No.: 16/478,794

(22) PCT Filed: Jan. 15, 2018

(86) PCT No.: PCT/ES2018/070027
§ 371 (c)(1),
(2) Date: Jul. 17, 2019

(87) PCT Pub. No.: WO2018/134457
PCT Pub. Date: Jul. 26, 2018

(65) Prior Publication Data
US 2019/0366365 A1    Dec. 5, 2019

(30) Foreign Application Priority Data
Jan. 18, 2017   (ES) ............................... ES201730055

(51) Int. Cl.
*B05B 7/32*   (2006.01)
*A61M 11/00*  (2006.01)
(Continued)

(52) U.S. Cl.
CPC ............... *B05B 7/32* (2013.01); *A61M 11/04* (2013.01); *B01J 13/0095* (2013.01);
(Continued)

(58) Field of Classification Search
CPC ........ B05B 7/32; B05B 12/004; A61M 11/04; A61M 11/001; A61M 11/02;
(Continued)

(56) References Cited

U.S. PATENT DOCUMENTS 5,884,846 A   3/1999  Tan
9,533,319 B1  1/2017  Kesavan et al.
(Continued)

FOREIGN PATENT DOCUMENTS

JP    2007-291503 A    11/2007

OTHER PUBLICATIONS

Ding, et al., A System to Create Stable Nanoparticle Aerosols from Nanopowders, J. Vis. Exp. 2016; 113: e54414, doi: 10.3791/54414, pp. 1-9 (Year: 2016).*
(Continued)

*Primary Examiner* — Daniel C. McCracken
(74) *Attorney, Agent, or Firm* — SEED INTELLECTUAL PROPERTY LAW GROUP LLP

(57) ABSTRACT

The object of the present invention relates to a nanoparticulate aerosol generator comprising a compressed gas reservoir (1) connected to a nanoparticulate material receptacle (2) through an operational valve (8'), wherein said receptacle (2) comprises an outlet hole (3) for the aerosol. Advantageously, the outlet of said nanoparticulate material receptacle (2) is connected to or inserted into a pressurized aerosol distribution chamber (4) equipped with a hole (9) for the exit of said aerosol out of the chamber (4). The invention provides the possibility of using different types of nanoparticles with sizes less than 100 nanometers continuously over (Continued)

time during long production periods of more than three hours. The invention also relates to a method for continuously generating nanoparticulate aerosols associated with the mentioned generator.

16 Claims, 3 Drawing Sheets

(51) Int. Cl.
    *A61M 11/02* (2006.01)
    *A61M 11/04* (2006.01)
    *B01J 13/00* (2006.01)
    *B05B 12/00* (2018.01)
    *B82Y 30/00* (2011.01)
    *B82Y 40/00* (2011.01)

(52) U.S. Cl.
    CPC .......... *B05B 12/004* (2013.01); *A61M 11/001* (2014.02); *A61M 11/02* (2013.01); *A61M 2205/3331* (2013.01); *A61M 2205/3334* (2013.01); *A61M 2205/75* (2013.01); *B82Y 30/00* (2013.01); *B82Y 40/00* (2013.01)

(58) Field of Classification Search
    CPC .. A61M 2205/3331; A61M 2205/3334; A61M 2205/75; A61M 2202/064; A61M 2205/7545; B01J 13/0095; B01J 8/004; B82Y 30/00; B82Y 40/00
    See application file for complete search history.

(56) References Cited

U.S. PATENT DOCUMENTS

| 10,673,347 | B2 | 6/2020 | Sarnago Andía et al. |
| 2012/0091223 | A1 | 4/2012 | Yi et al. |
| 2012/0174915 | A1 | 7/2012 | Kraft et al. |
| 2018/0327701 | A1 | 11/2018 | Fernandez Ledesma et al. |
| 2020/0261718 | A1 | 8/2020 | Sarnago Andía et al. |

OTHER PUBLICATIONS

McCabe, Smith and Harriot, Unit Operations of Chemical Engineering, 5th Ed., McGraw-Hill 1993, pp. 1-1130 (Year: 1993).*

Clemente et al., "A versatile generator of nanoparticle aerosols. A novel tool in environmental and occupational exposure assessment," *Science of the Total Environment 625*:978-986, 2018.

Clemente et al., "A Versatile Primary Nanoparticle Aerosol Generator for Nanosafety Studies: Instantaneous Clouds and Continuous Streams," Nanosafety 2017, Saarbrücken, Germany, Oct. 11-13, 2017, 2 pages.

Clemente et al., "Fluidized Bed Generation of Stable Silica Nanoparticle Aerosols," *Aerosol Science and Technology 47*:867-874, 2013 (9 pages).

Ding et al., "Deagglomeration testing of airborne nanoparticle agglomerates: Stability analysis under varied aerodynamic shear and relative humidity conditions," *Aerosol Science and Technology 50*(11):1253-1263, 2016 (12 pages).

Ding et al., "Dustiness and Deagglomeration Testing: Interlaboratory Comparison of Systems for Nanoparticle Powders," *Aerosol Science and Technology 49*:1222-1231, 2015 (11 pages).

Fabre et al., "Modeling the size distribution in a fluidized bed of nanopowder," *Environ. Sci.: Nano 4*:670-678, 2017.

Stahlmecke et al., "Investigation of airborne nanopowder agglomerate stability in an orifice under various differential pressure conditions," *J Nanopart Res 11*:1625-1635, 2009.

Tiwari et al., "A Cost-Effective Method of Aerosolizing Dry Powdered Nanoparticles," *Aerosol Science and Technology 47*:1267-1275, 2013.

\* cited by examiner

NANOPARTICULATE-AEROSOL GENERATOR AND METHOD FOR CONTINUOUSLY GENERATING AEROSOLS, ASSOCIATED WITH SAID GENERATOR

FIELD OF THE INVENTION

The present invention is encompassed in the field of aerosol generation technologies. More specifically, the object of the invention relates to dry aerosol generating devices mainly intended for generating nanoparticulate aerosols, although they are also intended, without limitation, for producing aerosols with particle sizes exceeding nanometric scales.

BACKGROUND OF THE INVENTION

In the sector corresponding to generators for generating aerosols with small size particles, the devices existing on the market are mainly based on wet methods, such as nebulization. Nevertheless, one of the main problems relating to the use of these devices is the significant presence of impurities originating from the solvent in the produced aerosols. Another limitation of these devices is that it is impossible to produce aerosols with a high concentration of nanoparticles, or that these nanoparticles have diameters below the scale of 100 nm.

As regards dry nanoparticulate aerosol generators which the present invention encompasses, they offer technical solutions which overcome the limitations of generators that use wet production methods. Some examples of said devices are described below.

U.S. Pat. No. 8,881,997 B2 relates to a dry nanoparticulate aerosol generator using a fluidized bed for dispersing solid nanoparticles by means of vibration. The vibrating cylinder of said generator produces vibration which breaks up nanoparticle agglomerates, such that the solid nanoparticles in the resulting aerosol are dispersed and not agglomerated. The generator disclosed in document U.S. Pat. No. 8,881,997 B2 also comprises a Venturi disperser which prevents the nanoparticles from leaking to the surrounding as a result of a negative pressure produced inside the generator.

On the other hand, United States patent application US 2004/0009118 A1 describes a device and method for producing metal oxide nanoparticles. The method includes the dry generation of an aerosol with micrometric and nanometric scale oxide particles by means of producing a plasma with high temperature zones where the metal vaporizes, to later on be oxidized in a cold zone of the generator where it condenses into nanoparticles. Additionally, the invention described in said document includes a nanoparticle dispersion method consisting of making the material reservoir oscillate vertically, so agglomeration of the nanoparticles due to the vibration thereof is prevented. The method disclosed in US 2004/0009118 A1 furthermore allows continuous generation during limited time intervals, such that nanoparticles at a constant flow rate are produced in said periods, with the production of metal oxide nanoparticles with sizes comprised between 1 nm and 100 microns.

Finally, Chinese patent CN 103353411 B describes a mixed wet/dry system for the generation of quasi-monodispersed nanoparticulate aerosols. Said system operates continuously, keeping the properties of the aerosol stable and the produced nanoparticles may have a size less than 100 nanometers, by means of using a nebulizer, a spray chamber, and an atomizer with a cooler. Patent CN 103353411 B furthermore discloses an aerosol generating system including a dispersion dryer, whereby the particles are dried and dispersed prior to aerosol generation.

Although the preceding examples constitute valid alternatives for conventional wet generators, up until now the use thereof presents the limitation of having a low flexibility as regards the nature of the materials used as nanoparticles. This is due to the fact that the selection of materials greatly determines the specific designs of their associated generator devices, which prevents the application thereof in a large variety of compounds. Likewise, the mentioned dry aerosol generating devices and methods also have the drawback of reduced continuous aerosol production periods, typically with times in the order of one hour or less. This limits their application in toxicity studies or quality controls which require an aerosol with continuous properties during longer periods.

There is therefore a need on the market to provide alternatives for generating aerosols which maintain the advantages of the known dry generation techniques but furthermore provide the possibility of using different nanoparticulate materials, characteristic of wet techniques, and the capacity to produce said aerosols for long periods of time.

The present invention aims to solve said need by means of a novel aerosol generator and an associated method which uses different types of nanoparticles a with size less than 100 nanometers, and the generation properties of which are continuous over time during production periods of more than three hours.

BRIEF DESCRIPTION OF THE INVENTION

A main object of the present invention is therefore to provide nanoparticulate aerosol generators which allow the dry production of aerosols for long periods of time, with nanoparticles of any material and of a size equal to or less than that made available by means of dry generators known up until now.

As regards its applications, the generator object of the invention allows producing nanoparticulate aerosols which can preferably be used in eco-toxicity studies, toxicological research, quality control, dispersion studies, or medical applications, among others.

Specifically, the object of the invention relates to a nanoparticulate aerosol generator comprising a compressed gas reservoir connected to a nanoparticulate material receptacle through an operational valve, wherein said receptacle comprises an outlet hole for the aerosol. Advantageously, the outlet of said nanoparticulate material receptacle is connected to or inserted into a pressurized aerosol distribution chamber equipped with a hole for the exit of said aerosol out of the chamber. A generator which allows continuously distributing aerosols consisting of small sized nanoparticles for prolonged periods of time of more than 3 hours is thereby achieved.

In a preferred embodiment of the aerosol generator of the invention, the compressed gas reservoir receives a first source of gas flow subjected to controlled pressure. More preferably, the connection between said first source of gas flow and the reservoir is made through a dryer and/or a filter. The dry production of aerosols, the moisture and pressure properties of which can be very precisely controlled, is thereby achieved.

In another preferred embodiment of the invention, the compressed gas reservoir comprises a receptacle having a volume comprised between 30 and 50 cm$^3$, with gas stored at a pressure of 7-10 barg. Said gas preferably comprises air.

In another preferred embodiment of the invention, the distribution chamber comprises a controlled atmosphere chamber or a dispersion tube. More preferably, said dispersion tube is formed by a plurality of sections, wherein each section contains one or more holes for accessing the inside of the distribution chamber once it is assembled and the generator is in operation.

In another preferred embodiment of the invention, the ends of the pressurized distribution chamber consist of terminal closure sections, wherein the nanoparticulate material receptacle is inserted or connected through one of said terminal sections and a second source of gas flow at controlled pressure is connected through the other one of the terminal sections. More preferably, the connection of the second source of gas flow to the distribution chamber is made by means of a valve, a dryer, and/or a filter. The aerosol stored in the distribution chamber is thereby maintained at precise moisture and pressure conditions.

Having the same purpose, for another preferred embodiment of the invention the pressurized distribution chamber and/or the compressed gas reservoir comprise one or more working pressure control points. Likewise, in another additional embodiment the pressurized distribution chamber comprises one or more moisture sensors for monitoring the generated aerosol.

In another preferred embodiment of the invention, the aerosol generator comprises a third source of diluting gas flow at the outlet of the pressurized distribution chamber, optionally connected to a mass flow controller and/or a filter. Greater control over the final aerosol flow produced is thereby achieved. Having the same purpose, in another embodiment the aerosol generator comprises a measuring point for measuring the flow rate of released aerosol, wherein said measuring point comprises a rotameter optionally connected to a filter.

Another aspect of the invention relates to a method for continuously generating nanoparticulate aerosols by means of using a generator according to any of the embodiments herein described. Said method advantageously comprises performing the following steps:
a) introducing a gas flow in the generator, compressing it in the compressed gas reservoir where it is stored at controlled pressure;
b) instantaneously releasing the compressed gas from the reservoir causing it to go through the nanoparticulate material receptacle, generating an aerosol of said material and causing it to reach the pressurized distribution chamber through an outlet hole of said receptacle, said aerosol being stored in said chamber at controlled pressure;
c) continuously releasing the aerosol stored in the pressurized distribution chamber through a hole for the exit out of said chamber.

In a preferred embodiment of the invention, the method comprises repeating step a) as many times as desired to maintain aerosol supply to the distribution chamber.

Likewise, in another embodiment the method comprises:
filtering or drying the gas entering and/or exiting the compressed air reservoir and/or the distribution chamber;
monitoring the properties of the gas entering the compressed air reservoir and/or the distribution chamber; and/or
monitoring the properties of the aerosol exiting the generator.

In the scope of the present invention, the expression "comprises" must be interpreted, when it is applied to the relationship between a main element and other secondary elements, as said main element including or containing said secondary elements, but without excluding other additional elements.

DESCRIPTION OF THE DRAWINGS

To complete the description of the invention and for the purpose of helping to better understand the technical features thereof, a set of drawings is appended herein in which the following is depicted in an illustrative and non-limiting manner:

FIG. 1a shows the general design of the generator, whereas FIG. 1b shows an inner detail of said generator in which the nanoparticulate material receptacle is depicted inserted into the pressurized aerosol distribution chamber.

REFERENCE NUMBERS USED IN THE DRAWINGS

For the purpose of helping to better understand the technical features of the invention, the mentioned drawings are accompanied by a series of reference numbers where the following is depicted in an illustrative and non-limiting manner:

| | |
|---|---|
| (1) | Compressed gas reservoir |
| (2) | Nanoparticulate material receptacle |
| (3) | Outlet hole of the nanoparticulate material receptacle |
| (4) | Pressurized aerosol distribution chamber |
| (4') | Intermediate sections of the aerosol distribution chamber |
| (4") | Terminal sections of the aerosol distribution chamber |
| (5, 5', 5") | Gas flow inlets |
| (6, 6') | Incoming gas dryers |
| (7, 7', 7") | Incoming gas filter |
| (8, 8', 8", 8''') | Gas regulating/shut-off control valves |
| (9, 9') | Holes for accessing the pressurized distribution chamber |
| (10, 10') | Incoming gas pressure control points |
| (11) | Moisture sensors of the pressurized distribution chamber |
| (12) | Mass flow controller |
| (13) | Generated aerosol |
| (14) | Generated aerosol flow rate control point |

DETAILED DESCRIPTION OF THE INVENTION

A detailed description of the invention in reference to a preferred embodiment thereof is set forth below based on FIGS. 1-2 of the present document.

Figure 1A:
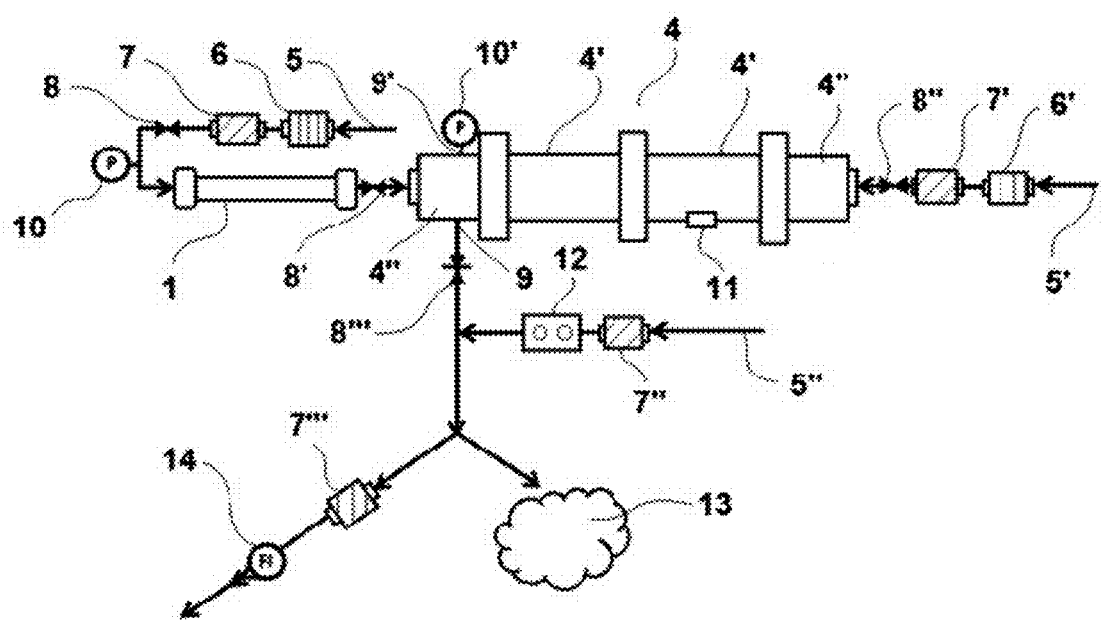
FIGS. 1a-1b show respective illustrative diagrams of the main elements of the generator of the invention according to a preferred embodiment thereof.
Figure 1B:
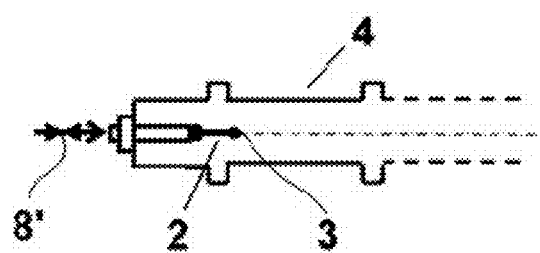

As shown in FIGS. 1a-1b, the present invention relates to a nanoparticulate aerosol generator essentially comprising a compressed gas reservoir (1) connected to a nanoparticulate material receptacle (2) (see detail in FIG. 1b), wherein said receptacle (2) comprises an outlet hole (3) connected to a pressurized aerosol distribution chamber (4). According to this configuration, the compressed gas reservoir (1) is a receptacle, for example a stainless steel receptacle, which can have a variable volume depending on the chosen application and receives a first source (5) of gas flow (said gas being, for example, air) subjected to controlled pressure. In an example of use for laboratory applications, said volume can be comprised between 30 and 50 cm$^3$, with air stored at a pressure of 7-10 barg. Preferably, the connection between the first source (5) of gas flow and the reservoir (1) is made through a dryer (6) and/or a filter (7) (for example, a HEPA or "High Efficiency Particle Arresting" filter), for the purpose of eliminating moisture from the air generator of the aerosol, as well as the impurities present therein. In other embodiments of the generator, it is also possible to provide a shut-off valve (8) between the first source (5) of gas flow and the reservoir (1), as means for regulating said flow.

As mentioned, the compressed gas reservoir (1) is connected to a nanoparticulate material receptacle (2). Said receptacle (2) comprises a container (FIG. 1b shows a cylindrical container, for example) equipped with an outlet hole (3) for releasing the nanoparticulate aerosol. Typically, for a cylindrical laboratory generator, said receptacle (2) has a length of between 80 and 120 mm, an inner diameter of between 5 and 20 mm, and an outlet hole (3) with an inner diameter between 1.0-1.4 mm. Preferably, the receptacle (2) is manufactured with stainless steel.

By means of the opening of another shut-off valve (8') arranged between the compressed gas reservoir (1) and the nanoparticulate material receptacle (2), the compressed gas is released instantaneously, driving said solid material through the outlet hole (3). The increased speed the gas experiences as it goes through the hole (3) gives rise to significant shearing forces which break up the agglomerates formed in the powder nanoparticulate material, releasing a cloud of nanoparticles of the desired scale.

For the purpose of providing the generator of the invention with the capacity to continuously supply the aerosol, the nanoparticulate material receptacle (2) is connected to or inserted into the pressurized distribution chamber (4), which allows keeping the aerosol, once generated, in the state of dispersion as a result of the inner pressure at which said chamber (4) is maintained. In different embodiments of the invention, the distribution chamber (4) can be, for example, a controlled atmosphere chamber or a dispersion tube. This second case is shown in the depiction illustrated by FIGS. 1a-1b, in which said dispersion tube consists of a chamber (4) formed by several (preferably stainless steel) sections (4'), for example, cylindrical sections, each of them with an inner diameter comprised between 8 and 12 cm and a height of 15-25 cm. Each section preferably contains one or more holes (9, 9') for accessing the inside of the chamber (4) once it is assembled and the generator is in operation. Likewise, the ends of the chamber (4) consist of corresponding terminal closure sections (4"). The nanoparticulate material receptacle (2) which will be used for generating the aerosols is inserted or connected through one of said terminal sections (4") (see FIG. 1b), whereas a second source (5') of gas flow which serves to maintain the inner pressure at different values, depending on the specific generation needs, is connected through the other one of the terminal sections (4"). The connection of said source (5') to the distribution chamber (4) is made, for example, by means of a valve (8"), optionally including the presence of a dryer (6') and/or a filter (7') (for example, a HEPA filter). It is possible to include one or more working pressure control points (10, 10') both in the pressurized distribution chamber (4) and in the compressed gas reservoir (1).

In the preferred embodiment illustrated in FIGS. 1a-1b, the total volume of the distribution chamber (4) is 8-10 liters once arranged with the nanoparticulate material receptacle (2) therein. Under normal working conditions, the chamber (4) can be kept at pressures comprised between 1 and 50 barg at the moment of ejecting the nanoparticulate aerosol therein. Once the aerosol has been generated and subjected to pressure, the opening of a valve (8''') connected to one of the holes (9) causes the exit thereof at the desired output concentration and flow rate in a continuous manner while said valve (8''') remains open.

In an optional embodiment of the pressurized distribution chamber (4), it can additionally include one or more moisture sensors (11) for monitoring the generated aerosols, thereby allowing precise control of the dry generation properties thereof.

In other additional embodiments of the invention, it is also possible to couple a third source (5") of gas flow to the outlet of the valve (8''') (optionally connected to a mass flow controller (12) and/or a filter (7")), which releases the aerosol out of the pressurized distribution chamber (4), using said third source (5") as means for diluting the final aerosol (13) released at the outlet of the pressurized chamber (5). Likewise, in other embodiments of the invention it is also possible to couple a measuring point (14) for measuring the flow rate of the final aerosol (13) released at the outlet of the pressurized chamber (5), said measuring point (14) comprising, for example, a rotameter optionally connected to a filter (7"). This provides different additional control systems for the properties of the aerosols generated with the invention, contributing to increased precision.

As described in the preceding paragraphs, the presence of the pressurized distribution chamber (5) provides the aerosol generator of the invention with two advantages. On one hand, it allows continuous supplying nanoparticulate aerosol having a stable concentration by means of actuating the valve (8''') for time periods of several hours, depending on the inner pressure values and the amount of material placed in the receptacle of the inner generator. On the other hand, nanoparticulate aerosols with a stable particle size distribution throughout the entire generation period, even after long periods of time, can be generated. This is due to the fact that the inner pressure of the tube and the disaggregation effect of the outlet valve (8''') prevents the aggregation of the nanoparticles contained inside the chamber (5), so a constant stream of small sized nanoparticles over time is achieved. The size of the nanoparticles generated in the aerosol exiting the complete system ultimately depends on the grain size of the starting material and its chemical nature, the system being highly versatile as regards these two parameters.

In short, the pressurized distribution chamber (5) allows controlling the concentration and particle size distribution in the aerosol stream. These two parameters are of great interest in all applications which entail the use of nanoparticulate aerosols in different technological fields, from the synthesis of gas phase materials to the validation of personal protection equipment in industrial hygiene, as well as in eco-toxicity studies, toxicological research of nanomaterials by inhalation, quality controls, dispersion studies, personal protection equipment and filter testing, calibration of nanoparticle measuring equipment, simulation of accidents involving nanomaterials, or medical applications.

Figure 2A:
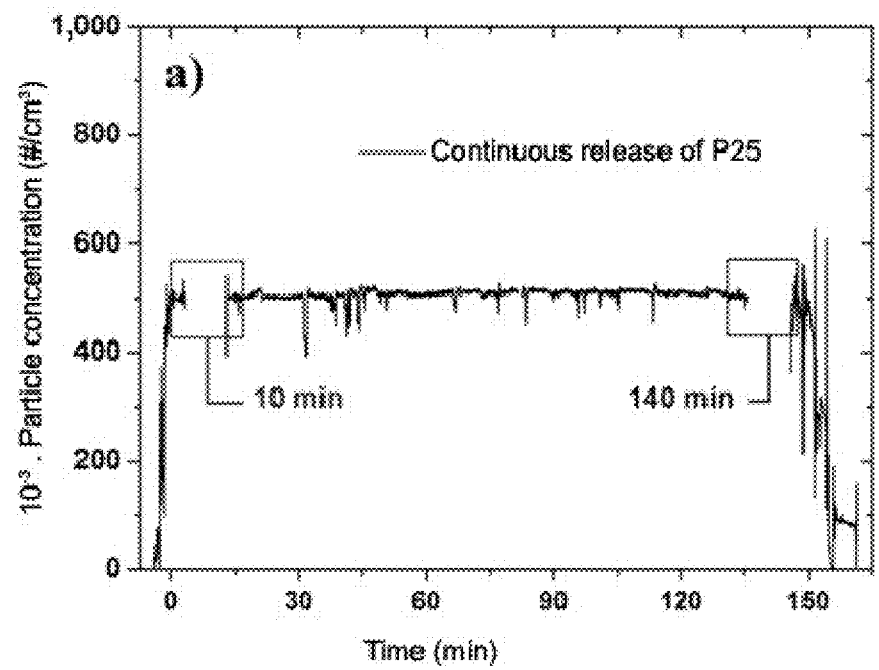
FIG. 2a shows a graph with the results of the total concentration of particles generated by the invention according to the preferred embodiment of FIGS. 1a-1b as a function of time and for nanoparticle size distributions taken after 10 and 140 min, after opening the outlet valve of the distribution chamber, using 25 mg of TiO$_2$ nanoparticles having a nominal diameter of 25 nm (Aeroxide P25, Evonik, Germany).
Figure 2B:
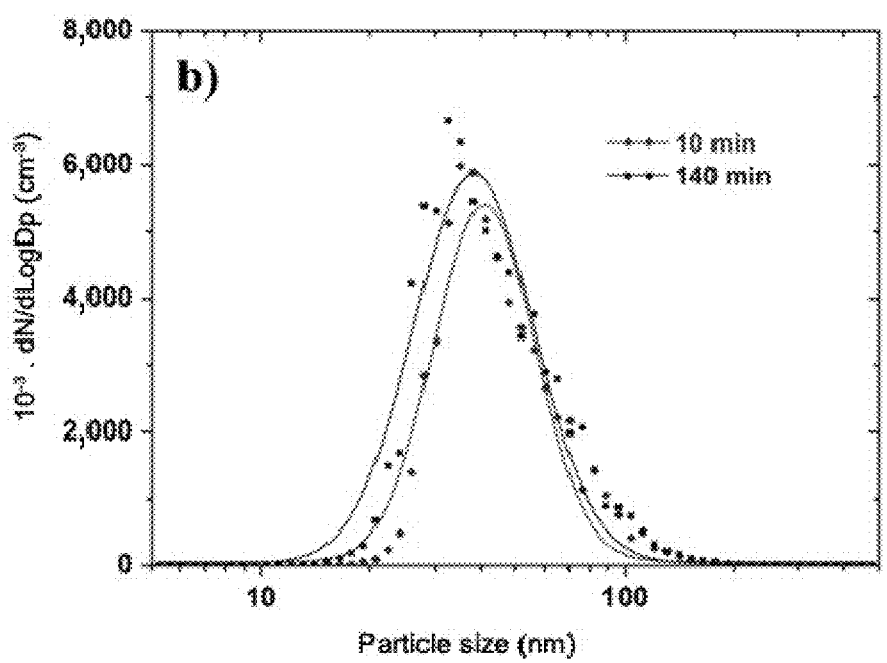
FIG. 2b shows a graph with the results of the concentration of particles (per cm$^3$) generated by the invention according to the preferred embodiment of FIGS. 1a-1b as a function of the size of said particles.

FIGS. 2a and 2b show the results of generating aerosols using 25 mg of $TiO_2$ nanoparticles having a nominal diameter of 25 nm (Aeroxide P25, Evonik, Germany) for a period of about 150 min, by means of using a generator according to the embodiment illustrated in FIGS. 1a-1b. It can be observed therein that the concentration of the particles in the aerosol stream (FIG. 2a) remains stable at about of $5.10^5$ #/$cm^3$ throughout the entire generation time, without any drop in this value being observed for more than two hours. The blank spaces in the concentration curve are due to the equipment for measuring the amount of material in the aerosol being used for determining the measurement of particle size distribution. These distributions, as can be observed in FIG. 2b, give similar average size and amplitude values, both at the beginning and end of the test. It must also be highlighted that the average size of the generated particles is about 50 nm, corresponding to small aggregates of 25 nm primary particles. These results therefore confirm that the aerosols generated with this system have a constant size and concentration for long periods of time.

Another aspect of the invention relates to a method for continuously generating nanoparticulate aerosols by means of using a generator according to any of the embodiments herein described. Said method preferably comprises the following steps:
a) introducing a gas flow in the generator, compressing it in the compressed gas reservoir (1) where it is stored at controlled pressure;
b) instantaneously releasing the compressed gas from the reservoir (1) causing it to go through the nanoparticulate material receptacle (2), generating an aerosol of said material and causing it to reach the pressurized distribution chamber (4) through an outlet hole (3) of said receptacle (2), said aerosol being stored in said chamber (4) at controlled pressure;
c) continuously releasing the aerosol stored in the pressurized distribution chamber (4) through a hole (9) for the exit out of said chamber.

The described method preferably comprises repeating step a) as many times as desired throughout said method to maintain aerosol supply to the distribution chamber (4).

Likewise, the method of the invention preferably comprises filtering or drying the gas entering and/or exiting the compressed air reservoir (1) and/or the distribution chamber (4).

Optionally, the properties of the gas entering the compressed air reservoir (1) and/or the distribution chamber (4) are monitored, and/or the properties of the aerosol exiting the generator are monitored.

As described above, the generation of the aerosol produced by means of the method of the invention can be kept continuous for times of more than 3 hours, with concentrations of particles in the nanometric scale or greater.

Figure 2C:
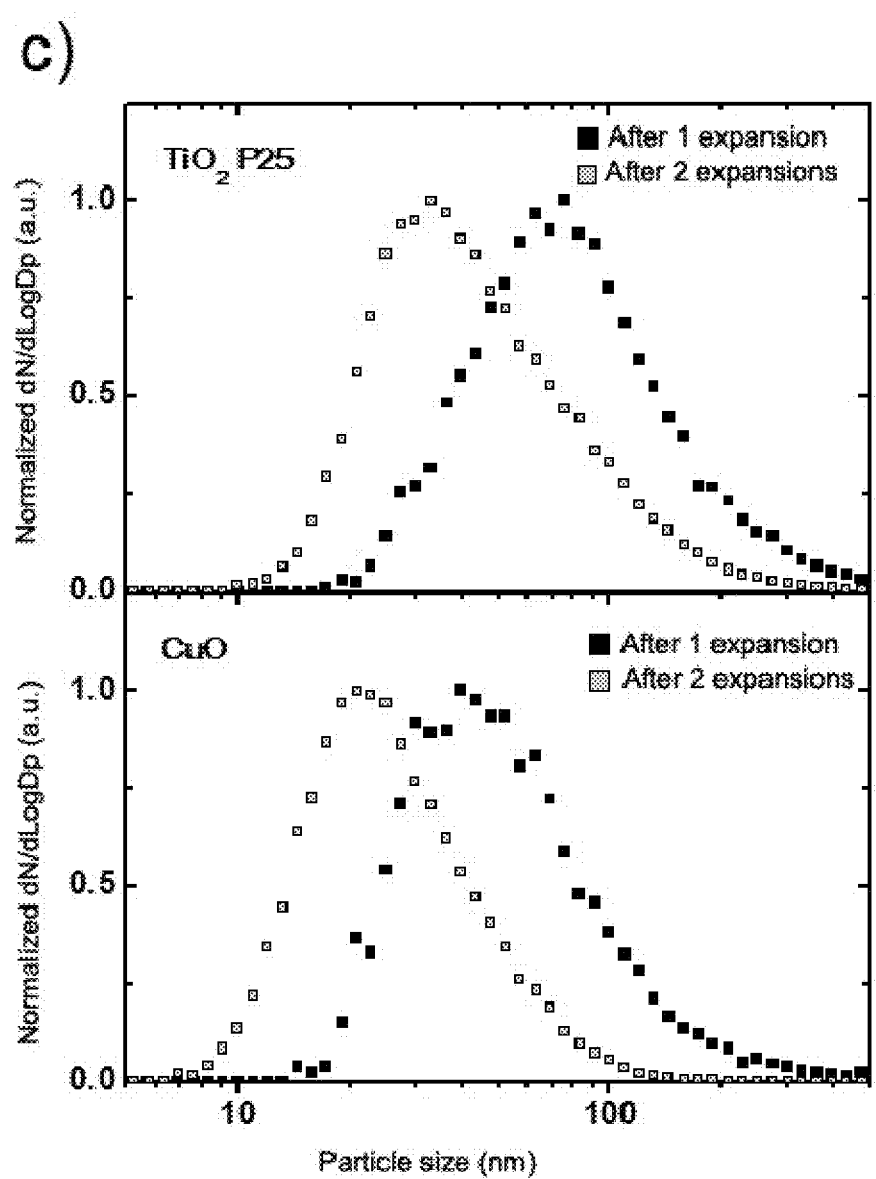
FIG. 2c shows nanoparticle size distributions in aerosol phase after one expansion and after two expansions through selected holes for different TiO$_2$ P25 and ZnO nanomaterials, performed by means of the generator of the invention.

FIG. 2c compares nanoparticle size distributions in the aerosol phase after one expansion and after two expansions through selected holes for different $TiO_2$ P25 and ZnO nanomaterials. These results confirm the effectiveness of the shearing force generated by the expansion for reducing the size of the nanoparticle aggregates in the aerosol. In this sense, an additional object of the present invention relates to the use of a generator or of a method for generating aerosols according to any of the embodiments herein described by means of a plurality of successive expansions of the gas in the compressed air reservoir (1).

The invention claimed is:

1. A nanoparticulate aerosol generator, comprising a compressed gas reservoir connected to a nanoparticulate material receptacle through a shut-off valve, wherein:
the nanoparticle material receptacle comprises an outlet hole for releasing nanoparticulate aerosol;
the generator further comprises a pressurized aerosol distribution chamber, in which the outlet hole of the nanoparticulate material receptacle is connected to or inserted into the pressurized aerosol distribution chamber;
the generator is configured such that by opening the shut-off valve, compressed air can instantaneously be released from the compressed gas reservoir to drive nanoparticulate material through the outlet hole into the pressurized aerosol distribution chamber;
the pressurized aerosol distribution chamber is adapted to maintain nanoparticulate aerosol at its interior within a controlled pressure, and the pressurized aerosol distribution chamber is equipped with an exit hole for the exit of the nanoparticulate aerosol out of the pressurized aerosol distribution chamber; and
ends of the pressurized aerosol distribution chamber consist of terminal closure sections, wherein the nanoparticulate material receptacle is inserted or connected through one of the terminal sections, and wherein a second source of gas flow at controlled pressure is connected through the other one of the terminal sections.

2. The nanoparticulate aerosol generator according to claim 1, wherein the compressed gas reservoir is connected to a first source of gas flow subjected to controlled pressure.

3. The nanoparticulate aerosol generator according to claim 2, wherein the connection between the first source of gas flow and the reservoir occurs through a dryer, a filter, or both.

4. The nanoparticulate aerosol generator according to claim 1, wherein the compressed gas reservoir comprises a receptacle having a volume between 30 $cm^3$ and 50 $cm^3$, with gas stored at a pressure of 7-10 barg.

5. The nanoparticulate aerosol generator according to claim 1, wherein the pressurized aerosol distribution chamber comprises a controlled atmosphere chamber or a dispersion tube.

6. The nanoparticulate aerosol generator according to claim 5, wherein the pressurized aerosol distribution chamber comprises a dispersion tube formed by a plurality of sections, wherein each section contains one or more holes for accessing the inside of the chamber once it is assembled and the generator is in operation.

7. The nanoparticulate aerosol generator according to claim 1, wherein the connection of the second source of gas flow to the pressurized aerosol distribution chamber occurs through a valve, a dryer, a filter, or combinations thereof.

8. The nanoparticulate aerosol generator according to claim 1, wherein the pressurized aerosol distribution chamber, the compressed gas reservoir, or both, comprises one or more working pressure control points.

9. The nanoparticulate aerosol generator according to claim 1, wherein the pressurized aerosol distribution chamber comprises one or more moisture sensors for monitoring the generated nanoparticulate aerosol.

10. The nanoparticulate aerosol generator according to claim 1, further comprising a third source of diluting gas flow at the outlet of the pressurized aerosol distribution chamber.

11. The nanoparticulate aerosol generator according to claim 10, wherein the third source of diluting gas flow is connected to a mass flow controller or a filter, or both.

12. The nanoparticulate aerosol generator according to claim 1, further comprising a measuring point for measuring a flow rate of the nanoparticulate aerosol released at the outlet of the pressurized aerosol distribution chamber.

13. The nanoparticulate aerosol generator according to claim 12, wherein the measuring point comprises a rotameter connected to a filter.

14. A method for continuously generating nanoparticulate aerosols by using a generator according to claim 1, the method comprising:
   a) introducing a gas flow in the generator, compressing the gas in the compressed gas reservoir where it is stored at controlled pressure;
   b) instantaneously releasing the compressed gas from the compressed gas reservoir causing it to go through the nanoparticulate material receptacle, generating the nanoparticulate aerosol and causing it to reach the pressurized aerosol distribution chamber through the outlet hole of the nanoparticle material receptacle, such that the nanoparticulate aerosol is stored in the pressurized aerosol distribution chamber at the controlled pressure; and
   c) continuously releasing the nanoparticle aerosol stored in the pressurized aerosol distribution chamber through the exit hole out of the pressurize aerosol distribution chamber.

15. The method for continuously generating nanoparticulate aerosols according to claim 14, comprising repeating step a) continuously to maintain supply of the nanoparticulate aerosol to the pressurized aerosol distribution chamber.

16. The method for continuously generating nanoparticulate aerosols according to claim 14, comprising:
   i) filtering or drying the gas entering or exiting, or both, the compressed air reservoir or the pressurized aerosol distribution chamber, or both; or
   ii) monitoring properties of the gas entering the compressed air reservoir or the pressurized aerosol distribution chamber, or both; or
   iii) monitoring properties of the nanoparticulate aerosol exiting the generator; or
   iv) any combination thereof.

* * * * *